(12) United States Patent
Stockton et al.

(10) Patent No.: US 11,436,238 B2
(45) Date of Patent: Sep. 6, 2022

(54) DATABASE, DATA STRUCTURES, AND DATA PROCESSING SYSTEMS FOR RECOMMENDING CLINICAL TRIAL SITES

(71) Applicant: Otsuka America Pharmaceutical, Inc., Rockville, MD (US)

(72) Inventors: Gwendolyn Stockton, Fenton, MI (US); Jehan Marino, New York, NY (US); Eva Kohegyi, Langhorne, PA (US); Judi Gidner, Yardley, PA (US); Kevin Derendorf, Princeton, NJ (US)

(73) Assignee: Otsuka America Pharmaceutical, Inc., Rockville, MD (US)

( * ) Notice: Subject to any disclaimer, the term of this patent is extended or adjusted under 35 U.S.C. 154(b) by 0 days.

(21) Appl. No.: 17/173,057

(22) Filed: Feb. 10, 2021

(65) Prior Publication Data

US 2021/0248150 A1 Aug. 12, 2021

Related U.S. Application Data

(60) Provisional application No. 62/972,543, filed on Feb. 10, 2020.

(51) Int. Cl.
*G06F 16/29* (2019.01)
*G06F 16/2457* (2019.01)
*G16H 10/20* (2018.01)
*G06F 16/9535* (2019.01)
*G06F 16/9538* (2019.01)

(52) U.S. Cl.
CPC ........ *G06F 16/24578* (2019.01); *G06F 16/29* (2019.01); *G06F 16/9535* (2019.01); *G06F 16/9538* (2019.01); *G16H 10/20* (2018.01)

(58) Field of Classification Search
CPC .......... G06F 16/24578; G06F 16/9535; G06F 16/9538; G06F 16/29; G16H 10/20
See application file for complete search history.

(56) References Cited

U.S. PATENT DOCUMENTS

2019/0355445 A1* 11/2019 Jones ............... G16H 10/20
2020/0410614 A1* 12/2020 Bonageri ........... G06N 20/20

* cited by examiner

*Primary Examiner* — Kris E Mackes
(74) *Attorney, Agent, or Firm* — Pillsbury Winthrop Shaw Pittman, LLP

(57) ABSTRACT

Methods, systems, and apparatuses, including computer programs, for generating a recommendation of candidate clinical trial sites. In one aspect, the method can include receiving parameters of a clinical trial, filtering, based on the received parameters, database data to obtain a filtered set of location-prescription pairs, generating a location-prescription data structure for each location-prescription pair, determining a ranking score, for each location-prescription pair, based on one or more prioritization parameters, identifying a subset of locations based on the respective ranking scores, obtaining a portion of map data from a map database that corresponds to a geographic region that is defined based on the identified subset of locations, and generating rendering data that, when rendered by a user device, causes the user device to render a visualization that includes (i) the obtained portion of the map data and (ii) data identifying the subset of locations on a display of a computer device.

20 Claims, 5 Drawing Sheets

DATABASE, DATA STRUCTURES, AND DATA PROCESSING SYSTEMS FOR RECOMMENDING CLINICAL TRIAL SITES

CROSS-REFERENCE TO RELATED APPLICATIONS

This application claims the benefit of U.S. Provisional Patent Application No. 62/972,543 filed Feb. 10, 2020, the entire contents of which is incorporated herein by reference in its entirety.

BACKGROUND

Selection of a clinical trial site is a critical part of the clinical trial process. Selection of a clinical trial site can impact a variety of factors related to the clinical trial's success including treatment (e.g., drug) indication approval timelines as well as a company's finances.

SUMMARY

According to one innovative aspect of the present disclosure, method for generating a visualization that presents a recommendation of one or more candidate sites for a clinical trial is disclosed. In one aspect, the method can include actions that include of receiving, by one or more computers, a request for a recommendation for a clinical trial site, the request for a clinical trial site including data that represents one or more parameters of the clinical trial, filtering, by one or more computers and based on the one or more parameters of the clinical trial, data from a plurality of databases to obtain a filtered set of location-prescription pairs, generating, by one or more computers, a location-prescription data structure for each location-prescription pair in the set of location-prescription pairs, determining, by one or more computers, a ranking score, for each location-prescription pair in the set of location-prescription pairs, based on one or more prioritization parameters, identifying, by one or more computers, a subset of one or more locations based on the respective ranking scores that correspond to each location-prescription pair of the set of location-prescription pairs, obtaining, by one or more computers, a portion of map data from a map database that corresponds to a geographic region that is defined based on the identified subset of one or more locations, and generating, by one or more computers, rendering data that, when rendered by a user device, causes the user device to render a visualization that includes (i) the obtained portion of the map data and (ii) data identifying the subset of one or more locations on a display of a computer device.

Other versions include corresponding systems, apparatus, and computer programs to perform the actions of methods defined by instructions encoded on computer readable storage devices.

These and other versions may optionally include one or more of the following features. For instance, in some implementations, filtering by one or more computers and based on the one or more parameters of the clinical trial, data from the plurality of databases to obtain a filtered set of location-prescription pairs can include generating, by one or more computers, a first query, wherein the first query includes first query parameters that are based on the one or more parameters of the clinical trial from the received request, executing, by one or more computers, the first query against a first database storing data records that describe attributes of historical clinical trials to obtain one or more attributes of the historical clinical trials that satisfy the first query, generating, by one or more computers, a second query, wherein the second query includes second query parameters based on the obtained one or more attributes of the historical clinical trials that satisfy the first query, and executing, by one or more computers the second query against a second database storing data records describing locations where prescriptions are being filled for a particular disease to obtain a plurality of location-prescription pairs that satisfy the second query.

In some implementations, each of the location-prescription pairs can include data identifying (i) a location and (ii) a prescription transaction.

In some implementations, the ranking score can be based on a number of times a prescription identified by the location-prescription pair was filled at a location identified by the location-prescription pair.

In some implementations, the one or more prioritization parameters can include (i) for each prescription filled at a location, a number of times the prescription was filled at the location, or (ii) for each prescription filled at a location, a number of individuals that have filled the prescription at the location.

In some implementations, the visualization that includes the data identifying the subset of one or more locations can include a visual characteristic that provides an indication of a rank of the location as a candidate for a clinical trial.

In some implementations, the visualization can include a heat map, the heat map identifying each location of the subset of locations by shading each of the locations with (i) one or more colors or (ii) one or more visual elements.

In some implementations, the method can further include ranking, by one or more computers, the plurality of location-prescription pairs based on the respective ranking scores for each location-prescription pair of the subset of location-prescription pairs.

Other aspects include corresponding methods, apparatus, and computer programs to perform actions of methods defined by instructions encoded on computer storage devices.

DETAILED DESCRIPTION

The present disclosure is directed towards generating recommendations for a location of a clinical trial site. In one aspect, a system and method can be employed that are configured to correlate data stored in one or more databases to identify and rank a plurality of candidate clinical trial sites. Then, one or more of the plurality of clinical trial sites can be selected for further evaluation as a clinical trial site based on the ranking. In some implementations, a site that is ranked the highest for a particular geographic region can be selected as a clinical trial site. In other implementations, one or more sites that have a ranking score that satisfies a predetermined threshold can be selected as candidate clinical trial site. In other implementations, a human user or intelligent software agent (e.g., machine learning model) can analyze ranking scores, other attributes, or a combination thereof, of a candidate clinical trial site and select one or more of the sites whose rankings scores, or other attributes, that have been analyzed for use as a clinical trial site.

The present disclosure provides the advantage of improving the relevance of a clinical trial using the intelligent clinical trial site selection techniques of the present disclosure. Intelligent site selection is achieved by making a selection of a particular clinical trial site from a set of one or more clinical trial site recommendations informed based on historical information related to a prescription transaction. This historical information can be used to generate a novel location-prescription data structure, some implementations, that includes data from multiple different data sources that can be analyzed, scored, and ranked in order to find one or clinical trial sites that are particularly suitable for a particular clinical trial. The location-prescription data structure can also be referred to herein as a location-prescription pair data structure or an LP-pair data structure.

The plurality of candidate clinical trial sites may be selected based on a variety of criteria. In some implementations, the plurality of clinical trial sites can be selected based on an evaluation of database data that indicates locations associated with a prescription transaction. In some implementations, the database data may also include a mapping of the particular therapeutic to one or more illnesses, conditions, or the like. In some implementations, the LP-pair data structure can include a logical grouping of fields structuring, ordering, or organizing data representing, or otherwise describing, a geographical location and a prescriptions transaction associated with the geographical location. In some implementations, however, the LP-pair data structure can also include data representing, otherwise describing, one or more other attributes of the prescription transaction, therapeutic, associated illness or condition, or any combination thereof.

Figure 1:
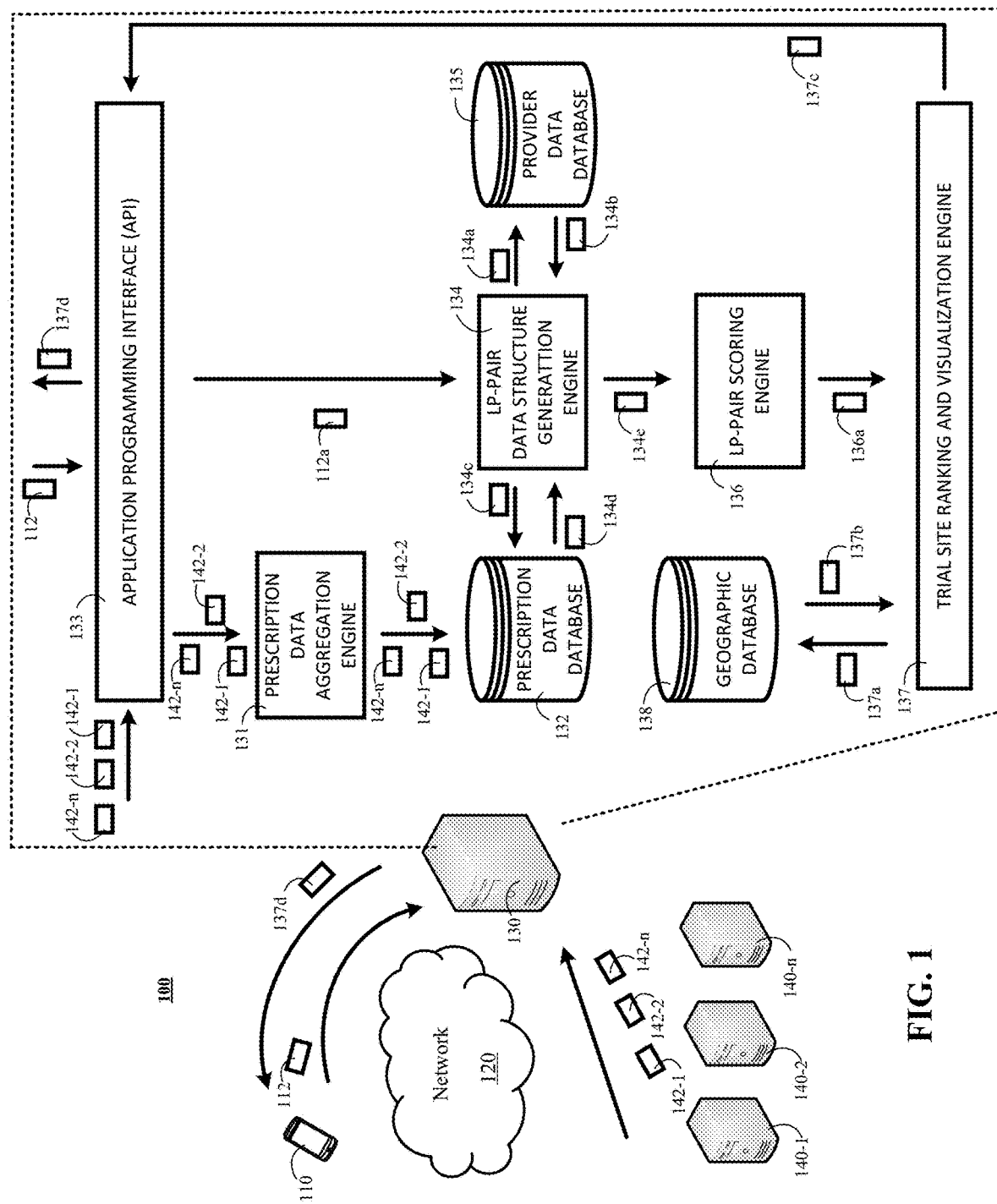
FIG. 1 is a block diagram of an example of a system for generating a set of prioritized locations for a clinical trial site.

FIG. 1 is a block diagram of an example of a system 100 for generating a set of prioritized locations for a clinical trial site. The system 100 can include a user device 110, a network 120, an application server 130, and one or more prescription data providers 140-1, 140-2. 140-$n$. The application server 130 can include a prescription data aggregation engine 131, a prescription data database 132, an application programming interface (API) engine 133, an LP-pair data structure generation engine 134, a provider-data database 135, an LP-scoring engine 136, a trial site ranking and visualization engine 137, and a trial site database 139. For purposes of this specification, the term engine can include one or more software components, one or more hardware components, or any combination thereof, that can be used to realize the functionality attributed to a respective engine by this specification.

A software component can include, for example, one or more software instructions that, when executed, cause a computer to realize the functionality attributed to a respective engine by this specification. A hardware component can include, for example, one or more processors such as a central processing unit (CPU) or graphical processing unit (GPU) that is configured to execute the software instructions to cause the one or more processors to realize the functionality attributed to a engine by this specification, a memory device configured to store the software instructions, or a combination thereof. Alternatively, a hardware component can include one or more circuits such as a field programmable gate array (FPGA), an application specific integrated circuit (ASIC), or the like, that has been configured to perform operations using hardwired logic to realize the functionality attributed to a engine by this specification.

With reference to the example of FIG. 1, the system 100 can include a plurality of prescription data providers 140-1, 140-2, 140-$n$. Each prescription data provider can include one or more computers that are each associated with a respective entity that is capable of writing a prescription, capable of filling prescriptions, capable of receiving prescription claims, or capable of processing prescription claims. Each of the respective entities can be located at different geographic locations. For purposes of this specification, each of the entities can include, for example, a pharmacist, pharmacy, doctor, doctor's office, or the like.

Each prescription data provider 140-1, 140-2, 140-$n$ can generate prescription data items such as prescription data items 142-1, 142-2, 142-$n$ and transmit the generated prescription data items to the application server 130 using the network 120. That is, the prescription data provider 140-1 can generate and transmit a prescription data item 142-1, the prescription data provider 140-2 can generate and transmit a prescription data item 142-2, and the prescription data provider 140-$n$ can generate and transmit prescription data item 142-$n$. Each prescription data item can be a data record that correspond to, or otherwise represent, a particular prescription transaction. A prescription transaction can include writing of a prescription, filling of a prescription, or filing or processing of a prescription claim. Each prescription data item 142-1, 142-2, 142-$n$ can include a data structure that includes one or more fields structuring data that represents or describes a location associated with a prescription transaction, data indicating a type of prescription associated with the prescription transaction, data indicating a therapeutic associated with the prescription transaction, data indicating an illness or condition associated with the prescription transaction, or the like.

A location associated with a prescription transaction can indicate a location where a prescription was written, location where a prescription was filled, or location where a prescription claim was filed or processed. A type of prescription transaction can indicate any type, category or classification of a prescription that was written, any type, category or classification of a prescription that was filled, or any type, category or classification of a prescription claim that was received or processed. A therapeutic associated with the prescription transaction can include a name of a drug or treatment prescribed by a written prescription, a name of a drug or treatment prescribed by a prescription that was filled, a name of a therapeutic of a prescription claim that was received, or a name of a therapeutic of a prescription claim that was processed. Data indicating an illness or condition associated with a prescription transaction can include an illness or condition that written prescription was issued to treat, an illness or condition that a filled prescription was filled to treat, an illness or condition treated by a prescription associated with a received prescription claim, or an illness or condition treated by a prescription associated with a prescription claim that was processed.

The prescription data aggregation engine 131 can aggregate prescription data 142-1, 142-2, 142-$n$, wherein n is any positive non-zero integer. In some implementations, the prescription data items 142-1, 142-2, 142-$n$ can be received via the application programming interface (API) 133 and provided, as an input, to the prescription data aggregation engine 131. In other implementations, the prescription data 142-1, 142-2, 142-n can be directly received by the prescription data aggregation engine 131. In some implementations, the prescription data aggregation engine 131 can obtain, parse and format the prescription data 142-1, 142-2, 142-n for storage in the prescription data database 131.

Parsing the prescription data 142-1, 142-2, 142-n for storage in the prescription data database 131 can include performance of a variety of different operations. For example, in some implementations, the prescription data aggregation engine 131 can process each prescription data item such as prescription data 142-1 and extract one or more particular portions of the prescription data item 142-1. For example, the prescription data aggregation engine 131 can process the prescription data item 142-1 to extract data indicating a location associated with a prescription transaction represented by the prescription data item 142-1.

The data extracted from the prescription data item 142-1 can be formatted and stored in the prescription data database 132. Formatting the prescription data item such as prescription data item 142-1 can include generating a data record for storage in the prescription database 132 that satisfies the database schema of the prescription database 132. For example, the data extracted from the prescription data item 142-1 can be obtained and stored into fields of a data record that satisfies the database schema of the prescription data database 132. This can include only using extracted data having a corresponding field in a newly generated record in the prescription database 132, with the fields of the generated record being defined by the database schema. Alternatively, or in addition, this can include formatting the data to be included in a particular field of the generated record to have a particular font, style, number of characters, or the like.

Each of the prescription data items 142-1, 142-2, 142-n can be received by application server 130 and processed by the prescription data aggregation engine 131 for storage in the prescription data database 132. The example of FIG. 1 describes a scenario where the prescription data items 142-1, 142-2, 140-n are received, processed, and stored in the prescription database 132 before receipt of the request 112 for clinical trial site recommendations, the present disclosure is not so limited. Instead, prescription data items can be received, processed, and stored before, during, and after receipt of this request 112 or other requests. However, any search or analysis of prescription data stored in the prescription data database 132 can only consider data extracted from prescription data items 142-1, 142-2, 142-n that have already been received, processed, and stored in the prescription data database 132.

In some implementations, a user device 110 can be used to generate a request 112 for clinical trial site recommendations. The request 112 can include one or more different parameters. The one or more parameters can include a target age range, a relevant indication, a therapeutic, or a combination thereof. For purposes of this specification, an indication can include a particular disease or condition to be treated during clinical trial. An example of an indication can include autism and an example of a therapeutic can include Abilify. Thus, in some implementations, an example request can include an age range of 12-16 years old, autism, and Abilify. However, the present disclosure is not limited to such example, Instead, data describing any age range, any indication, or any therapeutic can be included in the request 112. Moreover, there is no requirement that an age range, an indication, and a therapeutic or treatment need to be included in the request 112. Instead, any subset of these parameters may be included in the request 112. In yet other implementations, other parameters may be included in the request 112 such as gender, duration of condition, duration of medical regimen or treatment regimen, or the like. Thus, the request 112 for a clinical trial site recommendation can include any data that represents or describes an instruction, to the application server 130, to generate a one or more clinical trial site recommendations based on the parameters in the request 112.

The request 112 for clinical trial site recommendations can be transmitted, by the user device 110, to the application server 130 using the network 120. The user device can include a smartphone, a smartwatch, a tablet computer, a laptop computer, a desktop computer, or the like. The network 120 can include one or more wired Ethernet networks, one or more wired optical networks, one or more wireless Wi-Fi-networks, one or more LANs, one or more WANs, one or more cellular networks, the Internet, or any combination thereof.

The application server 130 can receive the request 112 for a clinical trial site recommendation using the API 133. The API 133 can include one or more software modules, one or more hardware modules, or a combination thereof, that can function as an interface between the application server 130 and the user device 110, the one or more prescription data providers 140-1, 140-2, 140-n, or a combination thereof. The API 133 can obtain the request 112 for a clinical trial site recommendation and generate an input 112a to the LP-Pair data structure generation engine 134. The input 112a to the LP-pair data structure generation engine 134 can include all, or a portion of, the request 112 formatted for input to the LP-Pair data structure generation engine 134. For example, the input 112a can include data describing the type of clinical trial to be performed that has been extracted from the request 112 and not include extraneous data such as header information that is used to transmit the request 112 from the user device 110 to the application server 130 using the network 120.

The LP-pair data structure generation engine 134 can generate an LP-pair data structure using data obtained from one or more databases 132, 135. Generating an LP-pair data structure can include filtering data in the one or more databases 132, 135 using parameters of the request 112 as data filters. The filtered data obtained from the one or more databases 132, 135, by the LP-pair data structure generation engine 134, can be aggregated into a data structure comprising one or more fields organizing logically related data that represents the filtered data. The one or more databases 132, 135 that are filtered to generate the LP-pair data structure can include a prescription database 132 and a provider data database 135.

The provider database 135 is a database that stores data describing historical clinical trial studies. This data can be obtained from multiple different data sources. For example, in some implementations the data stored in the provider database 135 can be obtained from a publicly available database such as the database at www.clinicaltrials.gov. In such instances, such clinical trial data may be generally available to anyone having a user device, internet access, and any necessary account credentials that facilitate connection to and access of the publicly available database. By way of another example, in some implementations, the data stored in the provider database 135 can be obtained from a proprietary database such as a database that is only accessible to a particular business entity. In some implementations, the business entity may include the business entity that implements system 100. However, the present disclosure is not so limited and the provider database 135 can be configured to aggregate data from any proprietary database.

Regardless of whether the data source for the provider database 135 is a public database or proprietary database, the data obtained from such sources for storage in the provider database 135 that describe a clinical trial can include (i) data describing a therapeutic used in the clinical trial (e.g., name of therapeutic, type of therapeutic, or other properties of the therapeutic), (ii) data indicating an illness or condition associated person(s) participating in the clinical trial, (iii) an age range of persons participating in the clinical trial, (iv) a clinical trial site for the clinical trial, (v) a name of a person facilitating the clinical trial, or (vi) any combination thereof. In some implementations, a person facilitating the clinical trial can a doctor and the clinical trial site can be the doctor's office, a clinic or other location used by the doctor during the clinical trial, or the like. In some implementations, the data obtained from such data sources and stored in the provider database 135 can also include data describing relationships between different studies. In some implementations, relationships between different studies can include, for example, pooling trial sites by therapeutic area to aid in clinical trial site selection or recommendation. The computer 130, or other computer hosting the provider data database 135, can periodically aggregate data from one or more public data sources, one or more private data sources, or a combination thereof, using one or more networks. The provider database 135 is accessible to the LP-pair data structure generation engine 134.

The other database depicted in the example of FIG. 1 is the prescription data database 132. The prescription data database 132 can store aggregated prescription data from multiple different prescription data providers 140-1, 140-2, 140-n. The prescription data database 132 is accessible by the LP-pair data structure generation engine 134.

The LP-pair data structure generation engine 134 can obtain the input 112a. This can include, for example, accessing a memory location where the input 112a was previously stored by API 133. In some implementations, the request 112a may be the same as the request 112 received by the API 133. In other implementations, the request 112a may be different than the request 112. For example, in some implementations, the API 133 can generate a new request 112a that is in a format that the LP-pair data structure generation engine 134 is configured to input. In some implementations, the request 112a may only be parameters of the request 112 that are extracted from the request 112 by the API 133 and stored in a memory device. In some implementations, instead of obtaining the request 112a from a memory, the LP-pair data structure generation engine 134 can receive the request 112a from the API 133.

The LP-pair data structure generation engine 134 can generate one or more queries 134a, 134c that can be used to obtain data from the one or more databases 132, 135 that can be used to generate a LP-pair data structure. The one or more queries 134a, 134c generated by the LP-pair data structure generation engine 134 can function as dynamically generated filter to filter the data stored in the one or more databases 132, 135 to identify data from the one or more databases 132, 135 relevant to a clinical trial site recommendation based on the request 112. In some implementations, one or more generated queries 134a, 134c can include one or more of the parameters from the input data 112a. However, in other implementations, only a subset of the queries such as queries 134a may include parameters from the request 112 whereas the other queries 13c may include parameters derived from the results 134b of the first set of one or more queries 134a.

By way of example with reference to FIG. 1, the LP-pair data structure generation engine 134 can obtain the input 112a, extract one or more of the parameters of the input 112a such as a target age range, a particular indication, a therapeutic, or a combination thereof, and then generate a query 134a based on the extracted one or more parameters. Continuing with the example input previously described, the LP-pair data structure generation engine 134 can obtain input data specifying an indication of autism, age range of 12-16, and therapeutic Abilify and generate query 134a that has parameters of autism, ages 12-16, and Abilify. The LP-pair data structure generation engine 134 can execute the generated query 134a against the provider database 135 to identify aggregated data that was either (i) publicly available or (ii) stored in a proprietary database to obtain results 134b that include data describing prior clinical trials related to patients having an age range of 12-16 years old having autism that were treated with Abilify. In some implementations, the obtained results 134b can include data describing the geographic location of clinical trials for patients satisfying the parameters of query 134a.

The LP-pair data structure generation engine 134 can process the results 134b and generate a second set of one or more queries 134c that are to be executed against the prescription data database 132. In some implementations, the query 134c executed against the historical information in the prescription data database 132 can be the same as query 134a and based upon the parameters extracted from the input 124a. In other implementations, the query 134c executed against the historical information in the prescription data database 132 can include the parameters extracted from the input 124a, data extracted from the results 134b, or both. For example, in some implementations, a name of a doctor can be extracted from the results data 134b and used as a parameter in the query 134c.

In some implementations, the initial request 112 may not include a particular therapeutic. Instead, in such implementations, the initial request 112 may only include data specifying and age or age range, a disease or condition, or both. For example, an initial request 112 may include an age range of 20 to 25 and high blood pressure as an indication. In such implementations, the LP-pair data structure generation engine 134 can generate a first search query 134a that includes age range 20-25 as a parameter and high blood pressure as a parameter and execute the query 134a. Then, the LPL-pair data structure generation engine 134 can obtain data from the result 134b of the query 134a such as a name of a therapeutic used in publicly available or propriety clinical trials and use the name of the therapeutic in the query 134c. In such implementations, the LP-pair data structure generation engine 134 can execute the query 134c against the historical information in the prescription data database 132 to obtain search results 134d that include a set of one or more candidate locations where prescription transaction occurred for a prescribed therapeutic having the same, or sufficiently similar, name as the name of the therapeutic extracted from the search results 134b. A name may be sufficiently similar if, for example, the prescribed therapeutic name matches, within a predetermined error threshold, the extracted therapeutic name. In some implementations, an error threshold can be established as a threshold number or ratio of matching characters in the respective names, predetermined distances between vectors representing each of the respective names, or the like.

The LP-pair data structure generation engine 134 can obtain the location specified by each historical data record obtained in the search results 134b and associate the location with one or more attributes of the prescription specified by the input data 112a such as the name of a therapeutic, name of an indication, age range of participants in a potential clinical trial, or any combination thereof, to create a location-prescription pair. A location-prescription pair (or LP-pair) data structure can be generated for each location returned in the search results 134b. Thus, in some implementations, each of the LP-pair data structures can include a location and a prescription identifier such as a therapeutic name. In other implementations, the LP-pair data structures can include a location and an indication name, a location and data indicating whether the location was previously used for a clinical trial, a therapeutic name, a location, and a number of times a prescription transaction occurred at the location, a therapeutic name, a therapeutic name, a location, and a number of unique individuals used the location to initiate a prescription transaction, or the like. Indeed, an LP-pair data structure can be generated that includes any of the aforementioned data, or any other data describing historical prescription transactions, in any combination in order to describe a relationship between geographic locations and historical prescription transactions. The LP-pair data structure generation engine 134 can provide the generated LP-pairs 134e to the LP-pair scoring engine. In some implementations, the LP-pair data structure generation engine 134 can store the generated LP-pairs 134e in a memory device, which can be accessed by one or more other engines such as the LP-pair scoring engine 136 for further processing.

Though the example above describes a scenario where an LP-pair data structure is generated for each location, the present disclosure is not so limited. Instead, in some implementations, a single LP-data structure can be generated that has multiple LP records that each represent a particular location and its corresponding parameters describing the particular location.

The LP-pair scoring engine 136 can obtain the generated LP-pairs 134e. For example, in some implementations, the LP-pair scoring engine 136 can access the generated LP-pairs 134e from the one or more memory devices. The LP-pair scoring engine 136 can generate a ranking score for each LP-pair the generated by the LP-pair data structure generation engine 134. Each LP-pair can be its own respective data structure. Alternatively, each LP-pair can be a separate row or set of fields within a single data structure. However, such distinctions are being described for clarity and are largely conceptual, as even in the instance of a "single" data structure, the set of fields within the "single" data structure that correspond to a particular LP-pair can be managed by the system 100 as a data structure.

In some implementations, the ranking score for each LP-pair can be determined based on one or more prioritization parameters associated with the LP-pair. In some implementations, the one or more prioritization parameters may being maintained in a separate data structure that stores prioritization parameters for each location in the prescription data database. In other implementations, the one or more prioritization parameters may be parameters of the LP-pair data structure. The one or more prioritization parameters can include, for example, (1) data indicating a number of times the prescription was filled at the location, (2) data indicating a number of individuals that have filled the prescription at the location, (3) data indicating a location confidence score based on user feedback related to prescription transactions, (4) data indicating a number of individuals who have had clinic visits at the location, (5) data indicating a history of the site with a specified demographic (e.g., a historical confidence score the specific demographic as at the site, a number of visits from each respective demographic of one or more demographics, or the like), (6) data indicating a research interest in the location (e.g., a research interest score), (7) data indicating an age of individuals that visited the location or filled a prescription at the location, (8) a number of historical trials participated at the location, (9) population density of the location relative to investigator location, (10) data indicating whether the location is located in a geographic location without competing trial sites, (11) data indicating whether the location has previously worked with a particular company on a clinical trial or other endeavor, (12) data describing previous performance or compliance issues at the location, (13) data describing a number of prescription and diagnosis claims in investigator zip code, (14) or the like. The LP-pair scoring engine 136 can associate the generated ranking score for each LP-pair with its respective LP-pair. This can include, for example, adding the generated ranking score to a field of each LP-pair data structure. Alternatively, this can include storing the generated ranking score for each LP-pair data structure and using an identifier for each LP-pair data structure to map the particular LP-pair data structure to a corresponding ranking score for the LP-pair data structure. The LP-pair scoring engine 136 can store data representing the stored LP-pairs 136a in a memory device. The scored LP-pairs 136a can be used as an input to a the trial site ranking and visualization module 137.

The trial site ranking and visualization engine 137 can obtain the scored LP-pairs 136a. For example, the trial site ranking and visualization engine 137 can access data representing the scored LP-pairs 136a from a memory device. The trial site ranking and visualization engine 137 can rank the obtained LP-pairs 136a based on the score that is associated with each respective LP-pair to generate a set of prioritized locations for a clinical trial study. In some implementations, the trial site ranking and visualization engine 137 can select, based on the score associated with each LP-pair, a number of particular locations that have a corresponding score that satisfies a predetermined a threshold. In some implementations, satisfying a threshold can include exceeding threshold. However, in some implementations, satisfying a threshold can include falling below the threshold if, for example, the threshold and each corresponding parameter being compared to the threshold have been negated.

The trial site ranking and visualization engine 137 can query 137a geographic database 138 to obtain map data based on the locations in each LP-pair selected based on its rank. For example, the query 137a can include location parameters for each of the selected LP-pairs and receive, from the geographic database 138, map data for the geographic region associated with the location parameters. The trial site ranking and visualization engine 137 can generate rendering data rendering data, that when rendered by one or more computers, causes a computer such as user device 110 to generated visualizations representing (i) map data obtained from the geographic database 138 and (ii) data identifying the set of one or more clinical trial site locations. In some implementations, for example, the generated visualizations can include a map that includes a graphical element representing each location that corresponds to a selected LP-pair. In other implementations, the generated visualization can include a heat map that uses different color-codings that shade different regions of the displayed map in particular colors, with each color and its intensity indicating a likelihood that the shaded geographic region is a recommended trial site.

The trial site ranking and visualization engine 137 can provide the rendering data 137c to user device 110 via the API 133 and the network 120. The API 133 can transmit the rendering data 137c to the user device 110 using one or more messages 137d. In some implementations, the one or more messages 137d may be the same as the rendering data 137c. In other implementations, the one or more messages 137d may be a formatted version of the rendering 137c that is optimized for display on the user device 110. In some implementations, for example, the API 133 can be configured to transcode the rendering data 137c into a format 137d that is best-suited for display via a display of the user device 110. Such transcoding may be performed based on network 120 type, user device 110 type, user device 110 operating system type, computing capabilities of the user device 110, or any combination thereof. The user device can process the rendering data 137d, generate one or more visualizations that depict the prioritized locations for the clinical trial on a visualized map of a geographic region. In some implementations, this visualized map can include a heat map. A user of the user device can then determine a location for a clinical trial, based on the one or more visualizations.

In some implementations, one or more selectable controls may be provided in a graphical user interface associated with the visualization. In such implementations, a user manipulate the one or more selectable controls in order to interact with the visualized. By way of example, in some implementations, a selectable control can be provided that can be used to select or deselect attributes such as prescription data volume for a therapeutic class, prescription data volume for a specific therapeutic, claims data by ICD code or indication, age of persons associated with displayed prescription transaction data, prior clinical trial sites from internal database, external trial sites from an external site such as clinicaltrials.gov, current site status from internal database, or the like. The foregoing are merely examples and are not intended to limit the scope of the present disclosure. Instead, a selectable control can be provided that can be used to toggle any attribute of the visualization or underlying prescription transaction data.

Figure 2:
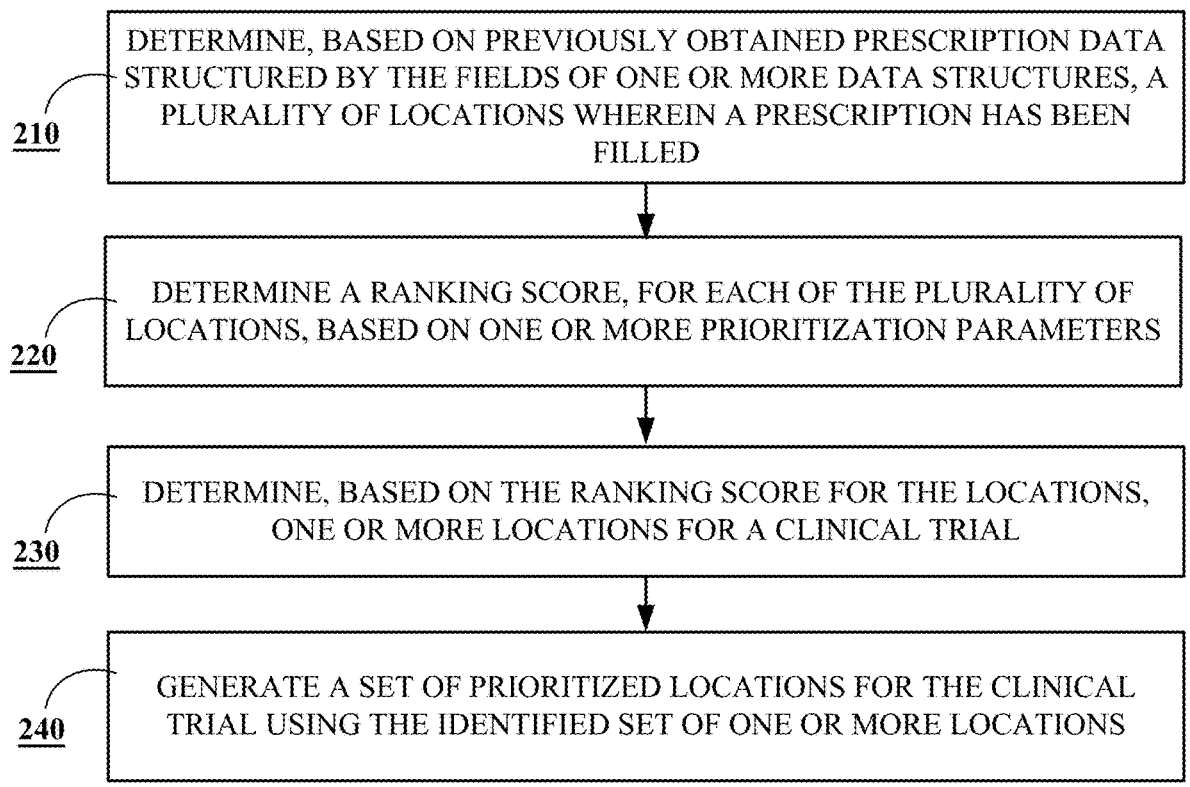
FIG. 2 is a flowchart of an example of a process for generating a set of prioritized locations for a clinical trial site.

FIG. 2 is a flowchart of an example of a process 200 for generating a set of prioritized locations for a clinical trial site. In some implementations, a process for generating a set of prioritized locations for a clinical trial site can include, for example, determining, based on previously obtained prescription data structured by fields of one or more data structures, a plurality of locations wherein a prescription for a therapeutic has been filled (210), determining a ranking score, for each of the plurality of locations, based on one or more prioritization parameters (220), determining, based on the ranking score for the locations, one or more locations for a clinical trial (230) and generating a set of prioritized locations for a clinical trial using the one or more locations (240).

Figure 3:
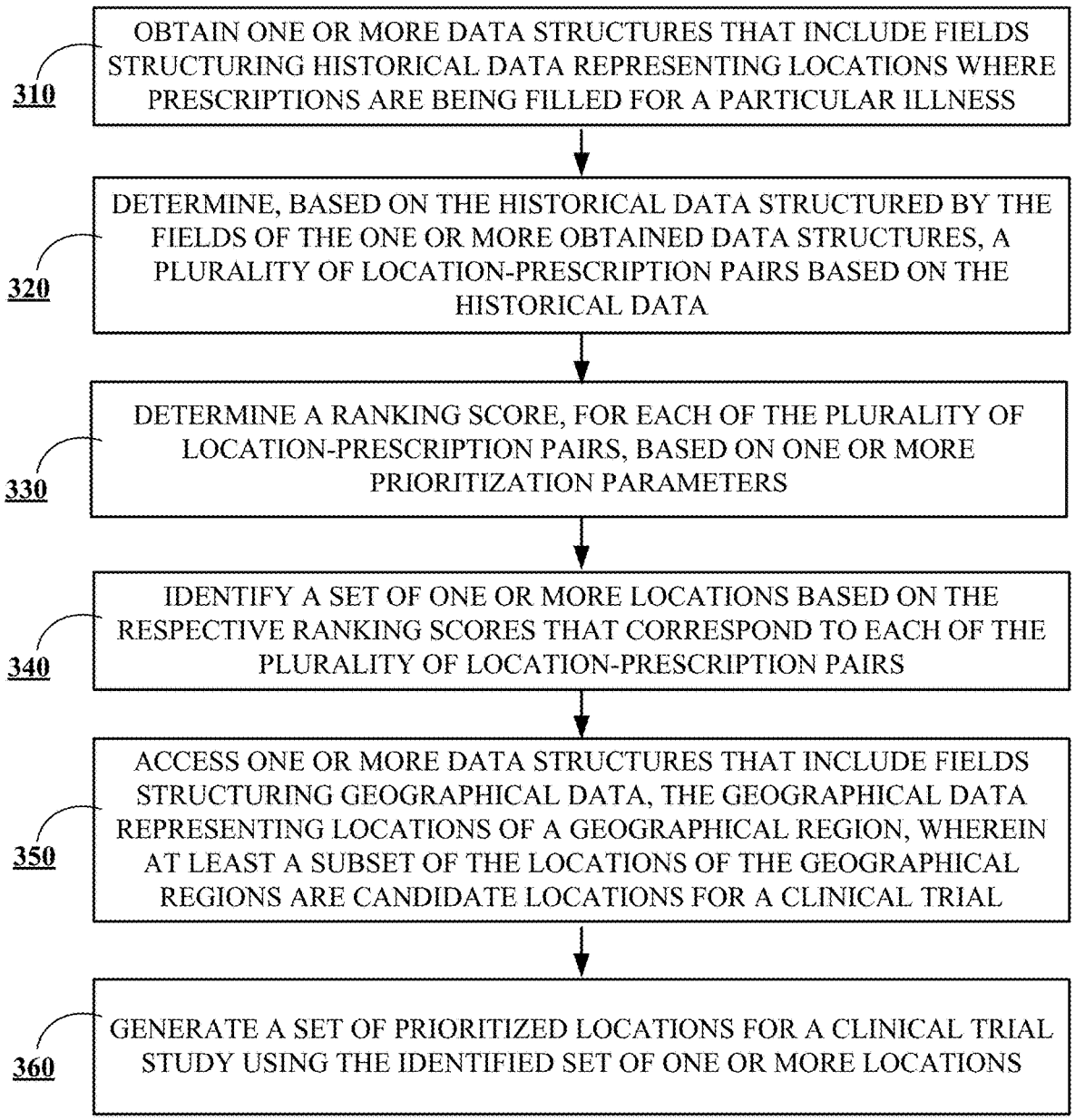
FIG. 3 is a flowchart of an example of another process for generating a set of prioritized locations for a clinical trial site.

FIG. 3 is a flowchart of an example of another process 300 for generating a set of prioritized locations for a clinical trial site. In some implementations, a process for generation a set of prioritized locations for a clinical trial site can include, for example, obtaining one or more data structures that include fields structuring historical data representing locations where prescriptions are being filled for a particular illness (310), determining, based on the historical data structured by the fields of the one or more obtained data structures, a plurality of location-prescription pairs based on the historical data (320), determining a ranking score, for each of the plurality of location-prescription pairs, based on one or more prioritization parameters (330), identifying a set of one or more locations based on the respective ranking scores that correspond to each of the plurality of location-prescription pairs (340), accessing one or more data structures that include fields structuring geographical data, the geographical data representing locations of a geographical region, wherein at least a subset of the locations of the geographical region are candidate locations for a clinical trial (350), and generating a set of prioritized locations for a clinical trial study using the identified set of one or more locations, wherein generating the set of prioritized sites for the clinical trial study includes rendering, by the one or more processors, (i) the geographical data and (ii) data identifying the set of one or more locations to generate a visualization on the display of a computer device, wherein the generated visualization visually identifies each of the prioritized locations in a map of a geographic region (360).

Figure 4:
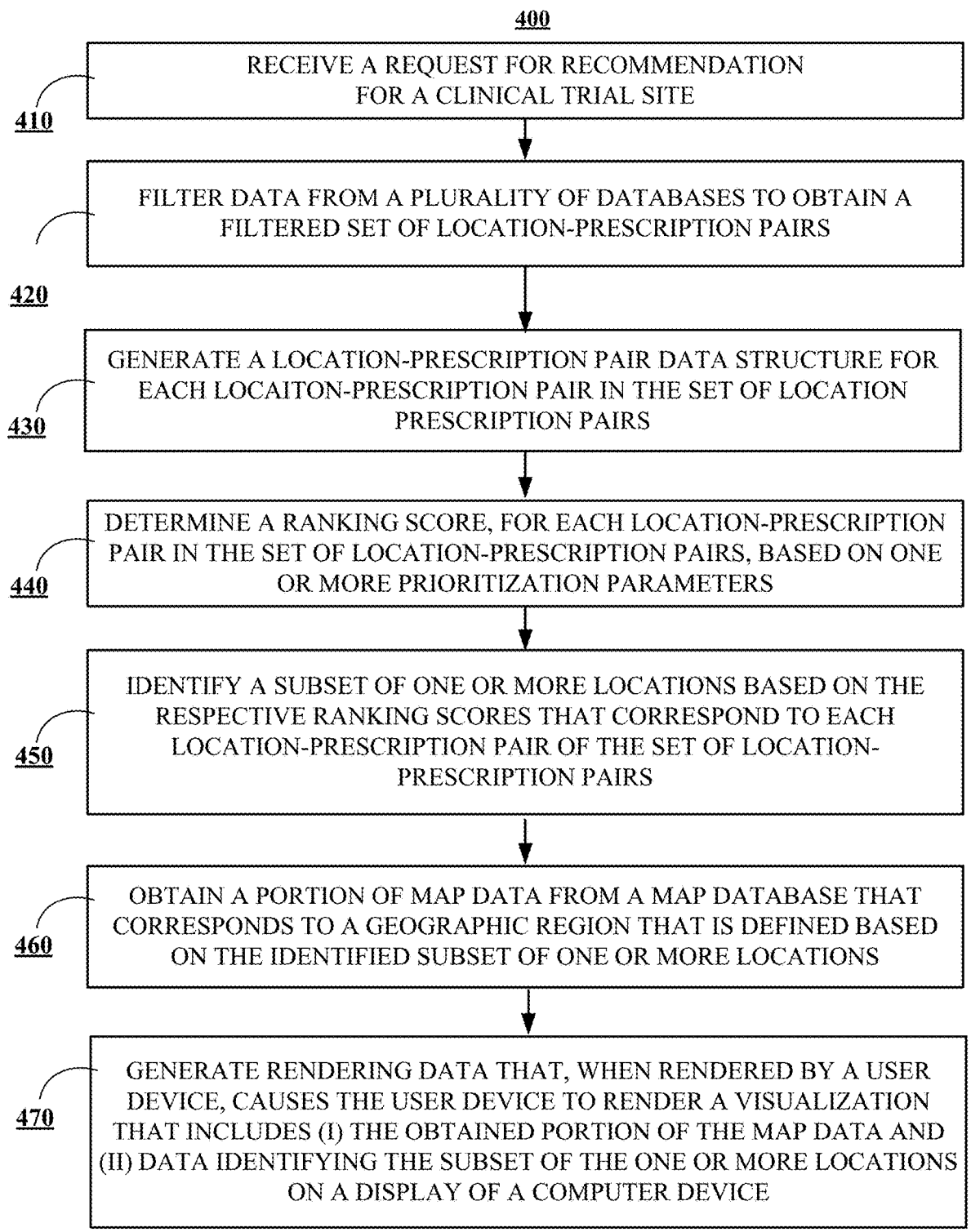
FIG. 4 is a flowchart of an example of another process for generating a set of clinical trial locations.

FIG. 4 is a flowchart of an example of another process 400 for generating a set of clinical trial locations. In some implementations, generating a set of clinical trial locations can include receiving, by the one or more computers, a request for a recommendation for a clinical trial site, the request for a clinical trial site including data that represents one or more parameters of the clinical trial (410), filtering, by the one or more computers and based on the one or more parameters of the clinical trial, data from a plurality of databases to obtain a filtered set of location-prescription pairs (420), generating a location-prescription data structure for each location-prescription pair in the set of location-prescription pairs that satisfy the second query (430), determining a ranking score, for each location-prescription pair in the set of location-prescription pairs, based on one or more prioritization parameters (440), identifying a subset of one or more locations based on the respective ranking scores that correspond to each location-prescription pair of the set of location-prescription pairs (450), obtaining a portion of map data from a map database that corresponding to a geographic region that is defined based on the identified subset of one or more locations (460), and generating rendering data that, when rendered by a user device, causes the user device to render a visualization that includes (i) the obtained portion of the map data and (ii) data identifying the subset of one or more locations on a display of a computer device (470).

Figure 5:
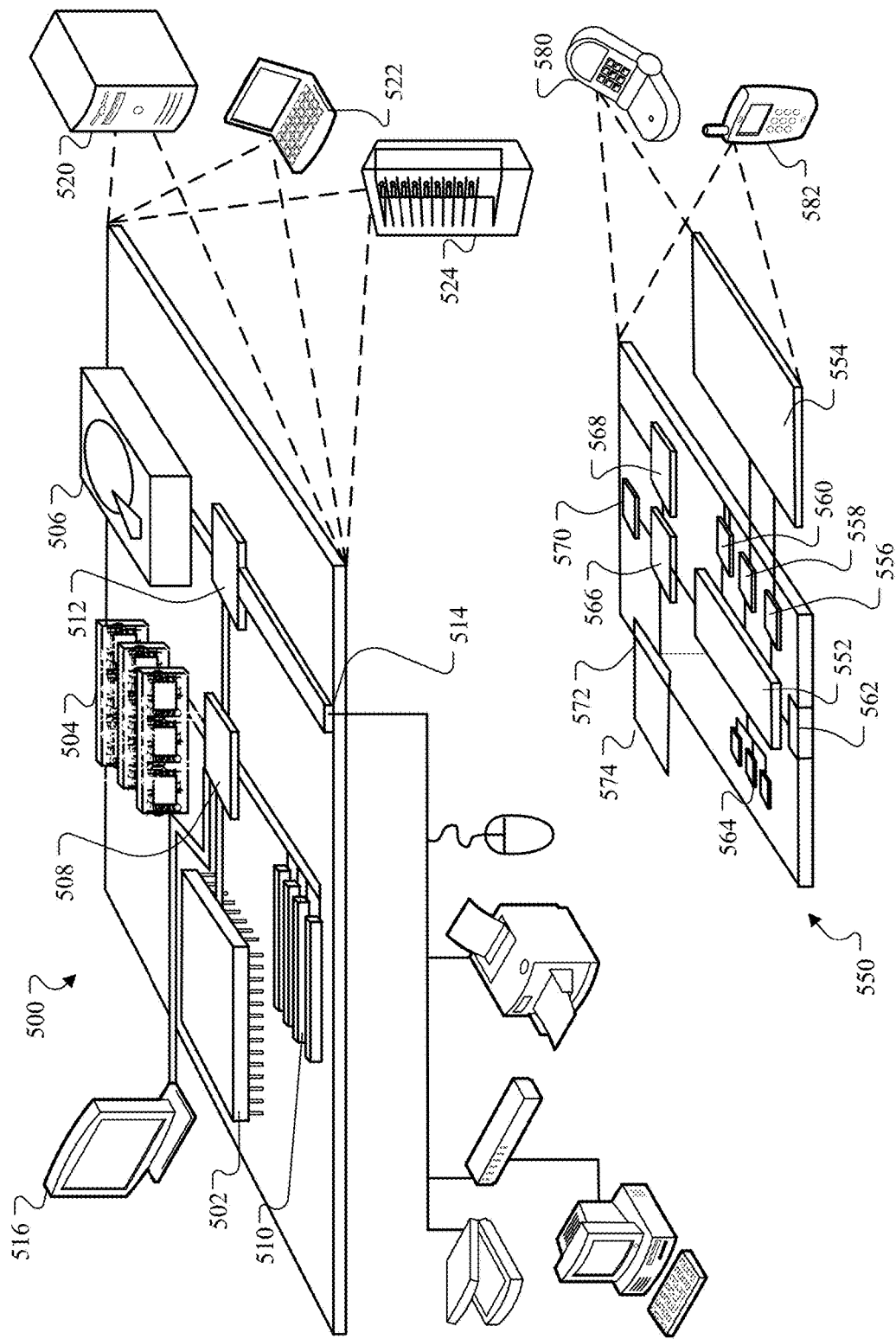
FIG. 5 is a block diagram of systems components that can be used to generate a a set of prioritized locations for a clinical trial site.

FIG. 5 is a diagram of system components that can be used to generate a set of prioritized locations for a clinical trial site.

Computing system 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, and other similar computing devices. Additionally, computing device 500 or 550 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 508. Each of the components 502, 504, 506, 508, 510, and 512, are interconnected using various busses, and can be mounted on a common motherboard or in other manners as appropriate. The processor 502 can process instructions for execution within the computing device 500, including instructions stored in the memory 504 or on the storage device 508 to display graphical information for a GUI on an external input/output device, such as display 516 coupled to high speed interface 508. In other implementations, multiple processors and/or multiple buses can be used, as appropriate, along with multiple memories and types of memory. Also, multiple computing devices 500 can be connected, with each device providing portions of the necessary operations, e.g., as a server bank, a group of blade servers, or a multi-processor system.

The memory 504 stores information within the computing device 500. In one implementation, the memory 504 is a volatile memory unit or units. In another implementation, the memory 504 is a non-volatile memory unit or units. The memory 504 can also be another form of computer-readable medium, such as a magnetic or optical disk.

The storage device 508 is capable of providing mass storage for the computing device 500. In one implementation, the storage device 508 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 504, the storage device 508, or memory on processor 502.

The high-speed controller 508 manages bandwidth-intensive operations for the computing device 500, while the low speed controller 512 manages lower bandwidth intensive operations. Such allocation of functions is only an example. In one implementation, the high-speed controller 508 is coupled to memory 504, display 516, e.g., through a graphics processor or accelerator, and to high-speed expansion ports 510, which can accept various expansion cards (not shown). In the implementation, low-speed controller 512 is coupled to storage device 508 and low-speed expansion port 514. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

Computing device 550 includes a processor 552, memory 564, and an input/output device such as a display 554, a communication interface 566, and a transceiver 568, among other components. The device 550 can also be provided with a storage device, such as a micro-drive or other device, to provide additional storage. Each of the components 550, 552, 564, 554, 566, and 568, are interconnected using various buses, and several of the components can be mounted on a common motherboard or in other manners as appropriate.

The processor 552 can execute instructions within the computing device 550, including instructions stored in the memory 564. The processor can be implemented as a chipset of chips that include separate and multiple analog and digital processors. Additionally, the processor can be implemented using any of a number of architectures. For example, the processor 510 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 550, such as control of user interfaces, applications run by device 550, and wireless communication by device 550.

Processor 552 can communicate with a user through control interface 558 and display interface 556 coupled to a display 554. The display 554 can be, for example, a TFT (Thin-Film-Transistor Liquid Crystal Display) display or an OLED (Organic Light Emitting Diode) display, or other appropriate display technology. The display interface 556 can comprise appropriate circuitry for driving the display 554 to present graphical and other information to a user. The control interface 558 can receive commands from a user and convert them for submission to the processor 552. In addition, an external interface 562 can be provided in communication with processor 552, so as to enable near area communication of device 550 with other devices. External interface 562 can provide, for example, for wired communication in some implementations, or for wireless communication in other implementations, and multiple interfaces can also be used.

The memory 564 stores information within the computing device 550. The memory 564 can be implemented as one or more of a computer-readable medium or media, a volatile memory unit or units, or a non-volatile memory unit or units. Expansion memory 574 can also be provided and connected to device 550 through expansion interface 572, which can include, for example, a SIMM (Single In Line Memory Module) card interface. Such expansion memory 574 can provide extra storage space for device 550, or can also store applications or other information for device 550. Specifically, expansion memory 574 can include instructions to carry out or supplement the processes described above, and can also include secure information. Thus, for example, expansion memory 574 can be provided as a security module for device 550, and can be programmed with instructions that permit secure use of device 550. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552 that can be received, for example, over transceiver 568 or external interface 562.

Device 550 can communicate wirelessly through communication interface 566, which can include digital signal processing circuitry where necessary. Communication interface 566 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 568. In addition, short-range communication can occur, such as using a Bluetooth, Wi-Fi, or other such transceiver (not shown). In addition, GPS (Global Positioning System) receiver module 570 can provide additional navigation- and location-related wireless data to device 550, which can be used as appropriate by applications running on device 550.

Device 550 can also communicate audibly using audio codec 560, which can receive spoken information from a user and convert it to usable digital information. Audio codec 560 can likewise generate audible sound for a user, such as through a speaker, e.g., in a handset of device 550. Such sound can include sound from voice telephone calls, can include recorded sound, e.g., voice messages, music files, etc. and can also include sound generated by applications operating on device 550.

The computing device 550 can be implemented in a number of different forms, as shown in the figure. For example, it can be implemented as a cellular telephone 580. It can also be implemented as part of a smartphone 582, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A data processing system for generating a visualization that presents a recommendation of one or more candidate sites for a clinical trial, the data processing system comprising:
    one or more processors; and
    one or more data storage mediums storing instructions, wherein the one or more processors are configured to execute the instruction to cause the one or more processors to:
        receive a request for a recommendation for a clinical trial site, the request including first data that represents one or more parameters of the clinical trial;
        filter, based on the one or more parameters of the clinical trial, second data from a plurality of databases to obtain a filtered set of location-prescription pairs;

generate a location-prescription data structure for each location-prescription pair in the filtered set of location-prescription pairs;
determine a ranking score, for each location-prescription pair in the filtered set of location-prescription pairs, based on one or more prioritization parameters;
identify a subset of one or more locations based on the respective ranking scores that correspond to each location-prescription pair of the filtered set of location-prescription pairs;
obtain a portion of map data from a map database that corresponds to a geographic region that is defined based on the identified subset of one or more locations; and
generate rendering data rendered by a user device to cause the user device to render a visualization that includes (i) the obtained portion of the map data and (ii) third data identifying the subset of one or more locations.

2. The data processing system of claim 1, wherein the second data being filtered comprises the one or more processors being further caused to:
generate a first query, wherein the first query includes first query parameters that are based on the one or more parameters of the clinical trial from the received request;
execute the first query against a first database storing data records that describe attributes of historical clinical trials to obtain one or more attributes of the historical clinical trials that satisfy the first query;
generate a second query, wherein the second query includes second query parameters based on the obtained one or more attributes of the historical clinical trials that satisfy the first query; and
execute the second query against a second database storing data records describing locations where prescriptions are being filled for a particular disease to obtain a plurality of location-prescription pairs that satisfy the second query, wherein the filtered set of location-prescription pairs comprises the plurality of location-prescription pairs that satisfy the second query.

3. The data processing system of claim 1, wherein each location-prescription pair of the filtered set of location-prescription pairs include data identifying (i) a location and (ii) a prescription transaction.

4. The data processing system of claim 1, wherein the ranking score is based on a number of times a prescription identified by the location-prescription pair was filled at a location identified by the location-prescription pair.

5. The data processing system of claim 1, where the one or more prioritization parameters include (i) for each prescription filled at a location, a number of times the prescription was filled at the location, or (ii) for each prescription filled at a location, a number of individuals that have filled the prescription at the location.

6. The data processing system of claim 1, wherein the visualization that includes the third data identifying the subset of one or more locations includes a visual characteristic that provides an indication of a rank of a location as a candidate for a clinical trial.

7. The data processing system of claim 1, wherein the visualization includes a heat map, the heat map identifying each location of the subset of locations by shading each of the locations with (i) one or more colors or (ii) one or more visual elements.

8. The data processing system of claim 1, wherein the one or more processors are further caused to:
rank the filtered set of location-prescription pairs based on the respective ranking scores for each location-prescription pair of the subset of location-prescription pairs.

9. A method for generating a visualization that presents a recommendation of one or more candidate sites for a clinical trial, the method comprising:
receiving, by one or more computers, a request for a recommendation for a clinical trial site, the request for a clinical trial site including data that represents one or more parameters of the clinical trial;
filtering, by one or more computers and based on the one or more parameters of the clinical trial, data from a plurality of databases to obtain a filtered set of location-prescription pairs;
generating, by one or more computers, a location-prescription data structure for each location-prescription pair in the filtered set of location-prescription pairs;
determining, by one or more computers, a ranking score, for each location-prescription pair in the filtered set of location-prescription pairs, based on one or more prioritization parameters;
identifying, by one or more computers, a subset of one or more locations based on the respective ranking scores that correspond to each location-prescription pair of the filtered set of location-prescription pairs;
obtaining, by one or more computers, a portion of map data from a map database that corresponds to a geographic region that is defined based on the identified subset of one or more locations; and
generating, by one or more computers, rendering data that, when rendered by a user device, causes the user device to render a visualization that includes (i) the obtained portion of the map data and (ii) data identifying the subset of one or more locations on a display of a computer device.

10. The method of claim 9, wherein filtering comprises:
generating, by one or more computers, a first query, wherein the first query includes first query parameters that are based on the one or more parameters of the clinical trial from the received request;
executing, by one or more computers, the first query against a first database storing data records that describe attributes of historical clinical trials to obtain one or more attributes of the historical clinical trials that satisfy the first query;
generating, by one or more computers, a second query, wherein the second query includes second query parameters based on the obtained one or more attributes of the historical clinical trials that satisfy the first query; and
executing, by one or more computers the second query against a second database storing data records describing locations where prescriptions are being filled for a particular disease to obtain a plurality of location-prescription pairs that satisfy the second query, wherein the filtered set of location-prescription pairs comprises the plurality of location-prescription pairs that satisfy the second query.

11. The method of claim 9, wherein each location-prescription pair of the filtered set of location-prescription pairs include data identifying (i) a location and (ii) a prescription transaction.

12. The method of claim 9, wherein the ranking score is based on a number of times a prescription identified by the location-prescription pair was filled at a location identified by the location-prescription pair.

13. The method of claim 9, where the one or more prioritization parameters include (i) for each prescription filled at a location, a number of times the prescription was filled at the location, or (ii) for each prescription filled at a location, a number of individuals that have filled the prescription at the location.

14. The method of claim 9, wherein the visualization that includes the data identifying the subset of one or more locations includes a visual characteristic that provides an indication of a rank of a location as a candidate for a clinical trial.

15. The method of claim 9, wherein the visualization includes a heat map, the heat map identifying each location of the subset of locations by shading each of the locations with (i) one or more colors or (ii) one or more visual elements.

16. The method of claim 9, the method further comprising:
ranking, by one or more computers, the filtered set of location-prescription pairs based on the respective ranking scores for each location-prescription pair of the subset of location-prescription pairs.

17. A non-transitory computer-readable medium storing instructions that, when executed by one or more computers, cause the one or more computers to:
receive a request for a recommendation for a clinical trial site, the request for a clinical trial site including data that represents one or more parameters of a clinical trial;
filter, based on the one or more parameters of the clinical trial, data from a plurality of databases to obtain a filtered set of location-prescription pairs;
generate a location-prescription data structure for each location-prescription pair in the filtered set of location-prescription pairs;
determine a ranking score, for each location-prescription pair in the filtered set of location-prescription pairs, based on one or more prioritization parameters;
identify a subset of one or more locations based on the respective ranking scores that correspond to each location-prescription pair of the filtered set of location-prescription pairs;
obtain a portion of map data from a map database that corresponds to a geographic region that is defined based on the identified subset of one or more locations; and
generate rendering data that, when rendered by a user device, causes the user device to render a visualization that includes (i) the obtained portion of the map data and (ii) data identifying the subset of one or more locations on a display of a computer device.

18. The non-transitory computer-readable medium of claim 17, wherein to filter, the instructions, when executed, further cause the one or more processors to:
generate a first query, wherein the first query includes first query parameters that are based on the one or more parameters of the clinical trial from the received request;
execute the first query against a first database storing data records that describe attributes of historical clinical trials to obtain one or more attributes of the historical clinical trials that satisfy the first query;
generate a second query, wherein the second query includes second query parameters based on the obtained one or more attributes of the historical clinical trials that satisfy the first query; and
execute the second query against a second database storing data records describing locations where prescriptions are being filled for a particular disease to obtain a plurality of location-prescription pairs that satisfy the second query, wherein the filtered set of location-prescription pairs comprises the plurality of location-prescription pairs that satisfy the second query.

19. The non-transitory computer-readable medium of claim 17, wherein each location-prescription pair of the filtered set of location-prescription pairs include data identifying (i) a location and (ii) a prescription transaction.

20. The non-transitory computer-readable medium of claim 17, where the one or more prioritization parameters include (i) for each prescription filled at a location, a number of times the prescription was filled at the location, or (ii) for each prescription filled at a location, a number of individuals that have filled the prescription at the location.

* * * * *